US00PP16424P2

(12) United States Plant Patent
Saul

(10) Patent No.: US PP16,424 P2
(45) Date of Patent: Apr. 11, 2006

(54) ***ECHINACEA* PLANT NAMED 'SUNSET'**

(50) Latin Name: *Echinacea hybrida*
Varietal Denomination: Sunset

(75) Inventor: Richard Saul, Cleveland, GA (US)

(73) Assignee: Itsaul Plants, Atlanta, GA (US)

( * ) Notice: Subject to any disclaimer, the term of this patent is extended or adjusted under 35 U.S.C. 154(b) by 132 days.

(21) Appl. No.: 11/041,619

(22) Filed: Jan. 22, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Echinacea* plant named 'Sunset', characterized by its upright and columnar plant habit; freely branching growth habit; large inflorescences with light red-colored ray florets and brownish orange-tipped receptacle spines; relatively early flowering habit; fragrant inflorescences; and good garden performance.

2 Drawing Sheets

Botanical designation: *Echinacea hybrida.*
Cultivar denomination: Sunset.

CROSS-REFERENCE TO RELATED APPLICATIONS

The present application is co-pending with the following related applications: *Echinacea* Plant Named 'Sunrise'; Richard Saul, applicant, U.S. Plant patent application Ser. No. 11/041,620.

BACKGROUND OF THE INVENTION

The present Invention relates to a new and distinct cultivar of *Echinacea* plant, botanically known as *Echinacea hybrida*, and hereinafter referred to by the name 'Sunset'.

The new *Echinacea* is a product of a planned breeding program conducted by the Inventor in Dahlonega, Ga. The objective of the breeding program is to develop new fragrant *Echinacea* cultivars with early flowering responses and unique ray floret coloration.

The new *Echinacea* originated from a cross-pollination made by the Inventor in July, 2002 of the *Echinacea purpurea* cultivar White Swan, not patented, as the female, or seed, parent with an unnamed selection of *Echinacea purpurea*×*Echinacea paradoxa*, not patented, as the male, or pollen, parent. The new *Echinacea* was discovered and selected as a single flowering plant by the Inventor in a controlled environment in Dahlonega, Ga. in June, 2003 from the resultant progeny of the stated cross-pollination. The new *Echinacea* was selected on the basis of its unique ray floret coloration.

Asexual reproduction of the new *Echinacea* by tissue culture was first conducted in Atlanta, Ga. in September, 2003. Since then, asexual reproduction by tissue culture has shown that the unique features of this new *Echinacea* are stable and reproduced true to type in successive generations.

SUMMARY OF THE INVENTION

The cultivar Sunset has not been observed under all possible environmental conditions. The phenotype may vary somewhat with variations in environment such as temperature and light intensity without, however, any variance in genotype.

The following traits have been repeatedly observed and are determined to be the unique characteristics of 'Sunset'. These characteristics in combination distinguish 'Sunset' as a new and distinct *Echinacea:*

1. Upright and columnar plant habit.
2. Freely branching growth habit.
3. Large inflorescences with light red-colored ray florets and brownish orange-colored receptacle spines.
4. Relatively early flowering habit.
5. Fragrant inflorescences.
6. Good garden performance.

Plants of the new *Echinacea* can be compared to plants of the female parent, the cultivar White Swan. In side-by-side comparisons conducted in Dahlonega, Ga., plants of the new *Echinacea* differed from plants of the cultivar White Swan in the following characteristics:

1. Plants of the new *Echinacea* were more compact than plants of the cultivar White Swan.
2. Plants of the new *Echinacea* flowered earlier than plants of the cultivar White Swan.
3. Plants of the new *Echinacea* had smaller inflorescences than plants of the cultivar White Swan.
4. Plants of the new *Echinacea* and the cultivar White Swan differed in ray floret coloration as plants of the cultivar White Swan had white-colored ray florets.

Plants of the new *Echinacea* can be compared to plants of the male parent selection. In side-by-side comparisons conducted in Dahlonega, Ga., plants of the new *Echinacea* differed from plants of the male parent selection in the following characteristics:

1. Plants of the new *Echinacea* had broader leaves than plants of the male parent selection.
2. Plants of the new *Echinacea* and the male parent selection differed in ray floret and receptacle spine coloration as plants of the male parent selection had dark yellow-colored ray florets and brown-colored receptacle spines.

Plants of the new *Echinacea* can be compared to plants of the *Echinacea* cultivar Art's Pride, not patented. In side-by-side comparisons conducted in Dahlonega, Ga., plants of the new *Echinacea* differed from plants of the cultivar Art's Pride in the following characteristics:

1. Plants of the new *Echinacea* were more freely branching than plants of the cultivar Art's Pride.
2. Plants of the new *Echinacea* had broader leaves than plants of the cultivar Art's Pride.
3. Ray florets of plants of the new *Echinacea* were broader and more imbricate than ray florets of plants of the cultivar Art's Pride.
4. Plants of the new *Echinacea* and the cultivar Art's Pride differed in ray floret coloration as plants of the cultivar Art's Pride had orange-colored ray florets.
5. Plants of the new *Echinacea* had larger discs than plants of the cultivar Art's Pride.

Plants of the new *Echinacea* can also be compared to plants of the *Echinacea* cultivar Sunrise, disclosed in U.S. Plant patent application Ser. No. 11/041,620. In side-by-side comparisons conducted in Dahlonega, Ga., plants of the new *Echinacea* differed from plants of the cultivar Sunrise in the following characteristics:

1. Plants of the new *Echinacea* were shorter and slightly less vigorous than plants of the cultivar Sunrise.
2. Plants of the new *Echinacea* had darker green-colored leaves than plants of the cultivar Sunrise.
3. Plants of the new *Echinacea* had smaller inflorescences, but larger discs than plants of the cultivar Sunrise.
4. Plants of the new *Echinacea* and the cultivar Sunrise differ in ray floret and receptacle spine coloration as plants of the cultivar Sunrise had pale yellow-colored ray florets and orange-colored receptacle spines.

BRIEF DESCRIPTION OF THE PHOTOGRAPHS

The accompanying colored photographs illustrate the overall appearance of the new *Echinacea* showing the colors as true as it is reasonably possible to obtain in colored reproductions of this type. Colors in the photographs may differ from the color values cited in the detailed botanical description which accurately describe the colors of the new *Echinacea*.

The photograph on the first sheet comprises a side perspective view of typical flowering plants of 'Sunset' grown in an outdoor nursery.

The photograph on the second sheet is a close-up view of typical inflorescences of 'Sunset'.

DETAILED BOTANICAL DESCRIPTION

The aforementioned photographs and following observations and measurements describe plants grown in Dahlonega, Ga., in an outdoor nursery under full sun conditions during the spring. When the plants were about one year old, the photographs, observations and measurements were taken. Plants used for the detailed description were grown in one-gallon containers. During the production of the plants, day temperatures ranged from 25 to 95° F. and night temperatures ranged from 0 to 70° F. Color references are made to The Royal Horticultural Society Colour Chart, 1995 Edition, except where general terms of ordinary dictionary significance are used.

Botanical classification: *Echinacea hybrida* cultivar Sunset.

Parentage:

*Female, or seed, parent.*—*Echinacea purpurea* cultivar White Swan, not patented.

*Male, or pollen, parent.*—Unnamed selection of *Echinacea purpurea*×*Echinacea paradoxa*, not patented.

Propagation:

*Type.*—By tissue culture.

*Root description.*—Fine, fleshy and freely branching; white, close to 155A, in color.

Plant description:

*Appearance.*—Perennial herbaceous container and garden plant. Upright and columnar plant habit; narrow inverted triangle. Freely basally branching; about six basal branches per plant. Moderately vigorous.

*Plant height.*—About 40 cm.

*Plant width or area of spread.*—About 22 cm.

*Basal branches.*—Length: About 38.5 cm. Diameter: About 5 mm. Internode length: About 4 cm. Aspect: Upright. Strength: Strong. Texture: Pubescent. Color: 144A overlain with close to 187A.

*Foliage description.*—Arrangement: Basal leaves, opposite; after flowering, alternate; simple. Length: About 11 cm. Width: About 3 cm. Shape: Lanceolate; elongated. Apex: Acuminate. Base: Attenuate. Margin: Entire. Venation pattern: Parallel. Texture, upper and lower surfaces: Pubescent; rough. Color: Developing and fully expanded foliage, upper surface: Darker than 147A. Developing and fully expanded foliage, lower surface: Close to 147B. Venation, upper and lower surfaces: Close to 146A. Petiole: Length: About 5 cm. Diameter: About 3 mm. Texture, upper and lower surfaces: Smooth; glabrous. Color, upper and lower surfaces: 144A overlain with close to 187A.

Inflorescence description:

*Appearance.*—Terminal inflorescences held above the foliage on strong peduncles. Composite inflorescence form, radially symmetrical; elongate oblong-shaped ray florets; disc florets massed at the center; ray and disc florets develop acropetally on the receptacle. Inflorescences persistent. Inflorescences face upright.

*Time of flowering.*—Long flowering period; plants flower freely from the late spring and continue to flower continuously until the autumn in Dahlonega, Ga.

*Postproduction longevity.*—Inflorescences maintain good color and substance for about two weeks on the plant.

*Quantity of inflorescences.*—One inflorescence per stem; about ten open inflorescences and flower buds per plant.

*Fragrance.*—Sweet; honey or rose-like.

*Inflorescence bud.*—Length: About 1 cm. Diameter: About 7.5 mm. Shape: Ovoid; conical. Color: Darker green than 147A.

*Inflorescence size.*—Diameter: About 6 cm. Depth (height): About 2.2 cm. Disc diameter: About 3.5 cm. Receptacle diameter: About 1 cm. Receptacle height: About 7.5 mm. Receptacle shape: Conical.

*Ray florets.*—Length: About 3.2 cm. Width: About 1 cm. Shape: Elongated oblong. Apex: Emarginate. Base: Attenuate. Margin: Entire. Texture, upper and lower surfaces: Smooth, glabrous; satiny; longitudinally ridged. Orientation: Initially upright and eventually slightly arching. Number of ray florets per inflorescence: About 22 in a single whorl. Color: When opening, upper surface: Close to 52C. When opening, lower surface: Close to 52D. Fully opened, upper surface: Close to 48D to close to 52D. Fully opened, lower surface: Close to 52D.

*Disc florets.*—Shape: Elongated tubular. Apex: Five-pointed; acute. Length: About 5 mm. Width: About 2 mm. Number of disc florets per inflorescence: Numerous; massed at the center of the inflorescence. Color: Immature: Close to 144A. Mature, apex and mid-section: Close to 144A to 144B. Mature, base: Close to 155D.

*Receptacle scales.*—Arrangement: One per disc floret; conspicuous, larger than disc florets. Length: About 1.1 cm. Diameter: About 1.5 mm. Shape: Elongate; spinescent; sharply acuminate. Texture: Stiff; smooth. Color: Apex: Close to 169A. Mid-section: Close to 144A. Base: Close to 155D.

*Phyllaries.*—Quantity per inflorescence: Numerous in about seven or eight whorls. Length: About 8 mm. Diameter: About 2.5 mm. Shape: Lanceolate. Apex: Acuminate. Base: Fused to receptacle. Margin: Entire. Texture, upper and lower surfaces: Pubescent. Color, upper and lower surfaces: Darker green than 147A.

*Reproductive organs.*—Androecium: Present on disc florets only. Stamen number: About five per floret. Anther shape: Elongated oblong. Anther size: About 3 mm by 1 mm. Anther color: Close to 202A. Pollen amount: Moderate. Pollen color: Close to 15A. Gynoecium: Present on both ray and disc florets. Pistil number: One per floret. Pistil length: About 7.5 mm. Stigma shape: Two-parted. Stigma color: Close to 3A.

*Seed/fruit.*—Seed and fruit development has not been observed.

Disease/pest resistance: Resistance to pathogens and pests common to *Echinacea* has not been observed on plants grown under outdoor conditions.

Garden performance: Plants of the new *Echinacea* have been observed to have good garden performance and to tolerate wind and rain. Plants of the new *Echinacea* have been observed to tolerate temperatures from 0 to 95° F.

It is claimed:

1. A new and distinct cultivar of *Echinacea* plant named 'Sunset', as illustrated and described.

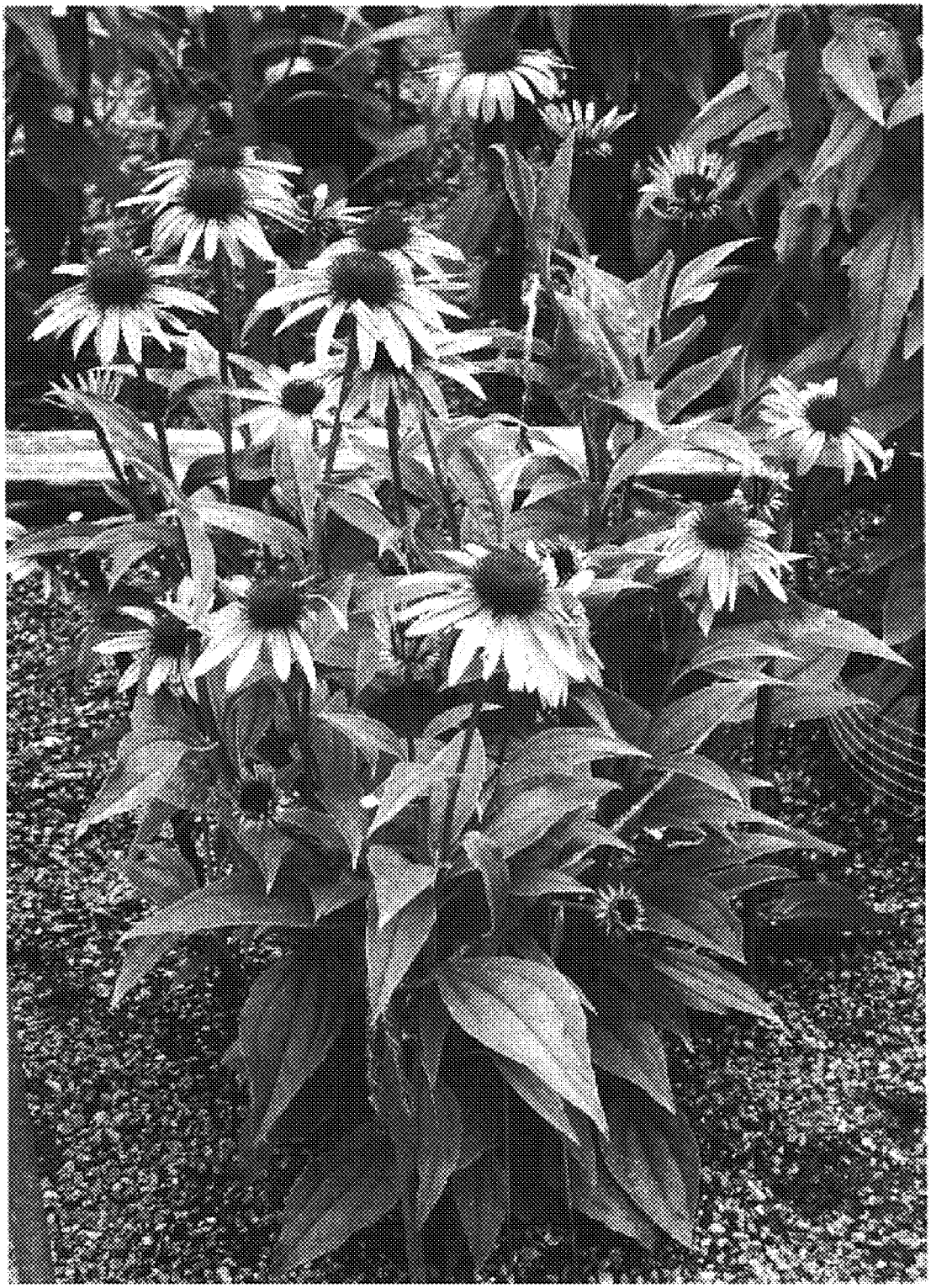

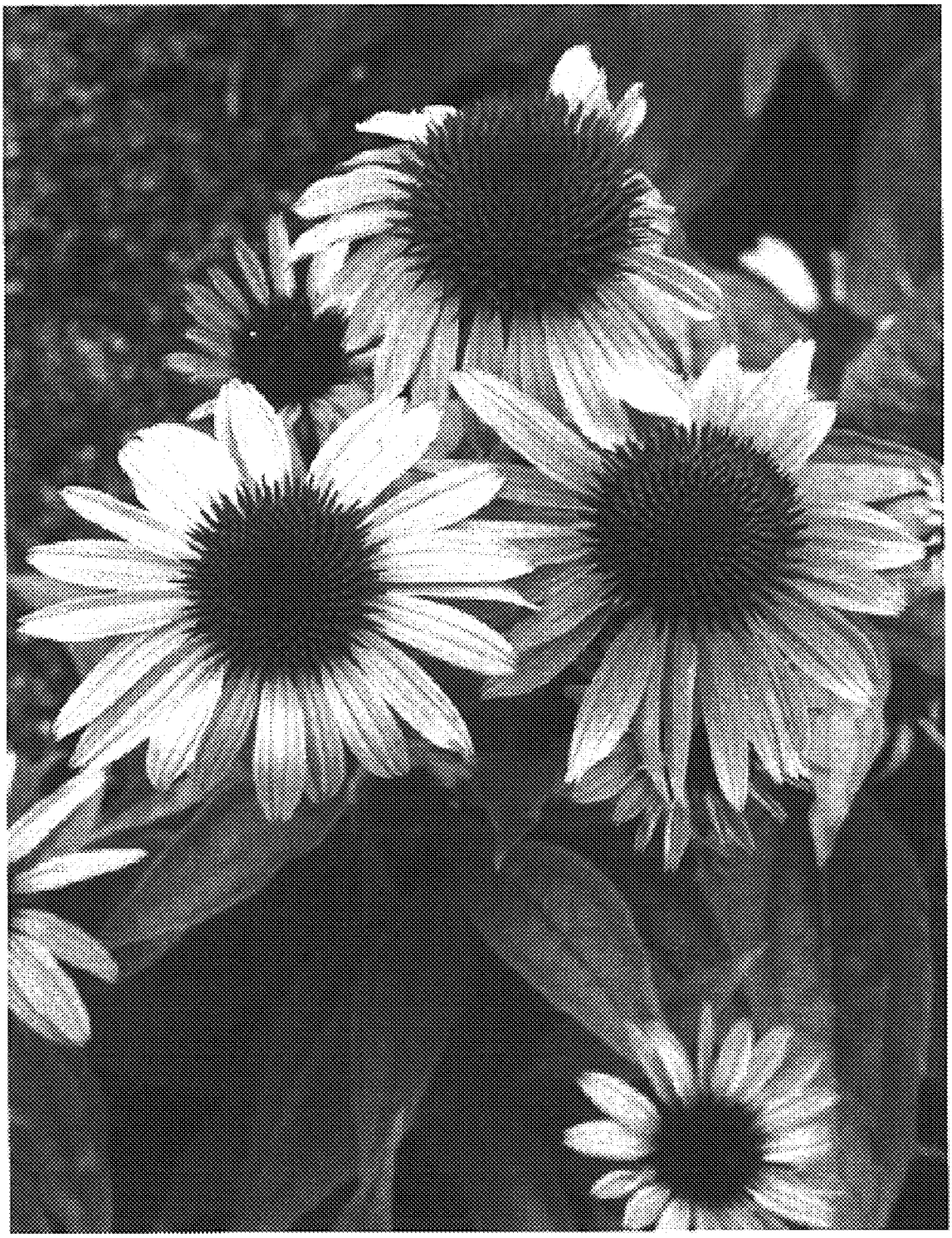

* * * * *